United States Patent [19]

Slaughter et al.

[11] Patent Number: 5,587,788

[45] Date of Patent: Dec. 24, 1996

[54] SAMPLING APPARATUS FOR INLINE SPECTROGRAPHIC ANALYSIS OF VISCOUS MATERIALS

[75] Inventors: John E. Slaughter, Richardson; George Olson, Plano, both of Tex.; William J. McShane, Arlington Heights, Ill.

[73] Assignee: Texas Instruments Incorporated, Dallas, Tex.

[21] Appl. No.: 589,812

[22] Filed: Jan. 22, 1996

Related U.S. Application Data

[63] Continuation of Ser. No. 378,903, Jan. 26, 1995, abandoned, which is a continuation of Ser. No. 98,554, Jul. 28, 1993.

[51] Int. Cl.$^6$ .................................................. G01N 21/01
[52] U.S. Cl. .............................................. 356/246; 356/440
[58] Field of Search ................................ 356/436, 440, 356/409, 246, 70, 244, 442; 250/576, 573, 570; 73/864, 864.44, 864.45

[56] References Cited

U.S. PATENT DOCUMENTS

| | | | |
|---|---|---|---|
| 4,090,789 | 5/1978 | Macemon | 356/244 |
| 4,135,100 | 1/1979 | Harada et al. | 356/440 |
| 4,451,152 | 5/1984 | Topol et al. | 356/440 |
| 4,692,620 | 9/1987 | Rosenthal | 356/440 |
| 4,893,935 | 1/1990 | Mandel et al. | 356/442 |
| 4,943,735 | 7/1990 | Nishikawa | 250/576 |
| 5,243,409 | 9/1993 | Sagner | 356/436 |

OTHER PUBLICATIONS

Bergquist, C. "How to Plan & Build Bookcases, Cabinets & Shelves" *Ortho Books*, copyright 1987, p. 40.

*Primary Examiner*—Richard A. Rosenberger
*Attorney, Agent, or Firm*—W. Daniel Swayze, Jr.; W. James Brady, III; Richard L. Donaldson

[57] ABSTRACT

A probe member (120) is slidably engaged by a sleeve (130) such that a sample of a fluid in a conduit (160) is movable from a position within a conduit to a second position outside of the conduit (160) and between a pair of fiber-optic bundles.

8 Claims, 2 Drawing Sheets

SAMPLING APPARATUS FOR INLINE SPECTROGRAPHIC ANALYSIS OF VISCOUS MATERIALS

This application is a continuation, of application Ser. No. 08/378.903, filed Jan. 26, 1995, now abandoned, which is a continuation, of application Ser. No. 08/098,554, filed Jul. 28, 1993.

TECHNICAL FIELD OF THE INVENTION

This invention relates to an apparatus and method for measuring the physical properties of a sample of a fluid which may be flowing in a conduit duct or being prepared in a vat.

BACKGROUND OF THE INVENTION

There are a number of different devices which are used for rapid, accurate spectrographic analysis of the reflectivity, transmissivity or transflectance of the samples. One such device is disclosed in U.S. Pat. No. 4,540,282 to Landa. This patent discloses that a device which enables immediate and rapid analysis of a number of different products. This type of device can measure three generalized types of information; the chemical constituents of a sample, the physical constituents of a sample and a quality of the sample. The chemical constituents of a product includes such things as the octane number in gasoline or the amount of aromatics in gasoline. In another environment, such items such as the amount of protein, starch, oil and other characteristics of the food may be measured. Yet another environment such blood constituents such as glucose or cholesterol can be measured using such a device. In the area of pharmaceuticals, the drug composition of a sample can be determined and such features such as the active zones of drugs can be measured. In the tobacco industry, the chemical characteristics such as nicotine, tar and methol can be measured using such device.

The second broad type of characteristics which can be measured using such a device are called physical parameters. Such physical parameters include physical characteristics such as the viscosity of liquids. In addition, the characteristics such as molecular weight or the multi-layer thickness of various coatings can be measured.

The third major area which can be measured using the device described in the Landa patent are "quality parameters" such as the degree of bake, for example, it may be necessary to determine when a cookie is properly cooked. One can use the spectral response from the cookie in the process of it being cooked to determine when to stop cooking.

Another area in which quality parameters can be measured involves, for example, adhesive strength. Another example of how the device disclosed in the Landa patent may be used in determining the taste of beers or wines. Since each of these products have a spectral signature, it is possible to determine the quality of wine by comparing the spectral signature of that wine with a known product or standard. For example, once the quality of a particular wine is known, it may be possible to take a spectral signature of that wine and determine what spectral characteristic or signature other wines must have in order to similarly have a good taste. Thereafter, other wines need not be taste-tested in order to determine that they are good wines. A spectral analysis need only be done and a signature be taken in order to determine such a characteristic.

Another example is that once the quality of a particular cheese is known, it may be possible to take a spectral signature of that cheese and determine what spectrographic characteristic or signature other cheeses may have in order to have a similarly good taste. Thus, other cheeses need not be taste-tested in order to determine that they are good cheeses. Similar to the wines, the spectral analysis need only be done on a signature viewing be taken in order to determine such characteristic.

There are basically three modes of introducing and detecting light from a sample. The first way is through reflectance. In the reflectance mode, the light is introduced into a sample by a probe. The light is then reflected back to the probe and the probe relays this information to the instrument which analyzes the light returned. Generally, this type of instrument will have a bi-directional fiber arrangement which enables light to move in two directions through the probe. With a reflective type of sample cell, the surface of this cell must be completely cleared of material between samples. With a reflective type, the infrared energy used to analyze the sample, penetrates approximately 5–10 micrometers into the material before the infrared energy is reflected or absorbed thus even a small amount of material remaining on the optical surface causes error in the measurement.

A second mode of operation is transmittance. In this mode, a first probe introduces light to a sample and a second probe will receive that light which has been transmitted through the sample. In this mode, two probes are necessary. One probe with this mode is that the sample could accumulate on the two probes, preventing fresh sample from passing between the probes and results in inaccurate reading.

The third mode of operation is transflectance mode. This mode is similar to the reflectance mode in that a bi-directional fiber is generally used which transmits and receives light from the sample. In this mode, light is introduced to the sample. Light which is reflected from the sample is returned through the probe and transmitted back to the instrument for analysis. The light which transmits to the sample is reflected by a mirror back to the sample and again through the probe and onto the instrument for analysis.

In order to obtain data for analysis, a probe may be inserted into a pipe to detect the constituents of a particular liquid product. If the probe is an optical rod surrounded by a sleeve, there can be a serious problem with the introduction of liquid between the rod and the sleeve. This occurs if there are problems with the seal which are tended to prevent liquid from flowing between the rod and sleeve. If such a problem occurs, the entire probe may be needed to be replaced. The reason that this is a serious problem in that each probe has particular characteristics. Therefore, by replacing one probe with another, the spectral signature which results may be altered as a function of the probe rather than a function of the material being analyzed.

Other probes in the art are made of the unitary structure. That is, an optical bundle or the like may be surrounded by an epoxy to the sleeve. Thus, any failure in the optical bundle requires replacement of the entire probe. Since each probe has a distinct personality, the reliability of data is decreased. The above-described unitary construction as an additional problem in that upon connecting the probe to the pipe or any other body a torque is necessarily required. If the probe is of unitary construction, any torque to the sleeve has a corresponding torque to the optical bundle. Such a torque can damage the probe, thus causing additional delays and costs.

Furthermore, U.S. Pat. No. 5,044,755 issued Sep. 3, 1991, to Landa discloses an optical rod or other device for propagating light, an optical barrel which in part surrounds the optical rod and the sleeve which is permitted to attach the probe to the source of light such as a fiber-optical bundle. This probe may be fitted with a bi-directional focusing adapter and a reflective tip.

OBJECTS OF THE INVENTION

It is an object of the present invention to provide a probe for the introduction and the receipt of light from a sample, the probe being nonsensitive to leaking. It is a further object of the invention to provide a probe which may be used with viscous samples such as cheeses or the like. It is another object of the invention to provide a probe which does not necessitate the use of a separate and distinct mirror. It is yet another object of the invention to provide a probe in which the light is not reflected. It is an object of the invention to provide a probe which maintains a constant light path and length of light traveling through the probe. It is an object of the invention to provide a probe such that the sample may be transported to the light path. It is an object of the invention to provide a fresh sample and with a minimum of old samples for each measurement of the sample.

SUMMARY OF THE INVENTION

In accordance with the purposes of the present invention, the present invention is a modular probe for use with a electro-optical device. The modularity of the probe allows for easy replacement of individual components of the probe without affecting the character of the probe. The probe includes a member to obtain a sample of the fluid. The member is coated with Teflon, for example polytetrofluroethylene of PTFE and is movably engaged with a Teflon coated sleeve so that the sample is moved to the position where light can be used to determine the characteristics of the sample. The member includes a transparent window to calibrate a measuring device. The present invention does not require a seal between the sleeve and the member as a result of the Teflon coating on both the sleeve and member, and the present invention provides a fresh sample each time the probe is inserted into the sample, maintaining the calibration of the system while obtaining accurate reading.

This present invention employs an inline sampling system which is a sanitary style, provides easy maintenance, and prevents system entrapment of material and be usable to the food industry by preventing direct contact of the food product with glass fibers.

In another aspect of the invention, a cylinder has external threads to engage a bolt and compress the sleeve. In another aspect of the invention, the cylinder has a flange at one end of the cylinder to engage with the flange of the conduit for conducting the fluid. In another aspect of the invention, a connecting arm is connected to the probe member so that the probe can be moved within the sleeve.

In another aspect of the invention, an actuator moves the probe within the sleeve.

In another aspect of the invention, the sleeve includes a mandrel to support the probe against the flow of the fluid, and the mandrel includes an aperture for allowing the fluid to flow past the probe.

The accompanying drawings, which are incorporated in and form a part of this specification illustrate the embodiments of the present invention, and together with the description, serve to explain the principles of the invention.

DETAILED DESCRIPTION OF THE INVENTION

Figure 1:
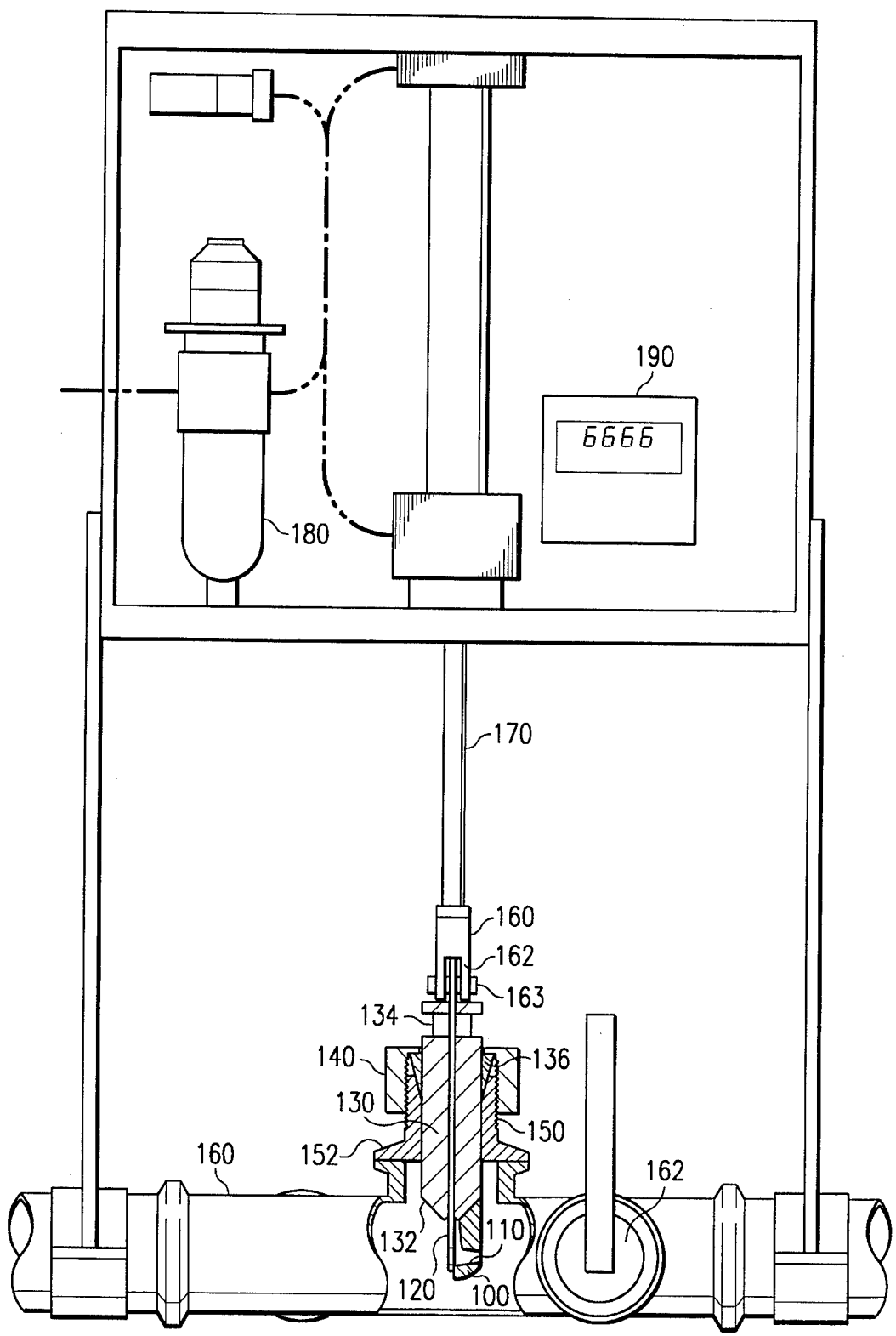
FIG. 1 is a schematic drawing of the probe being used in conjunction with the fluid.
Figure 2:
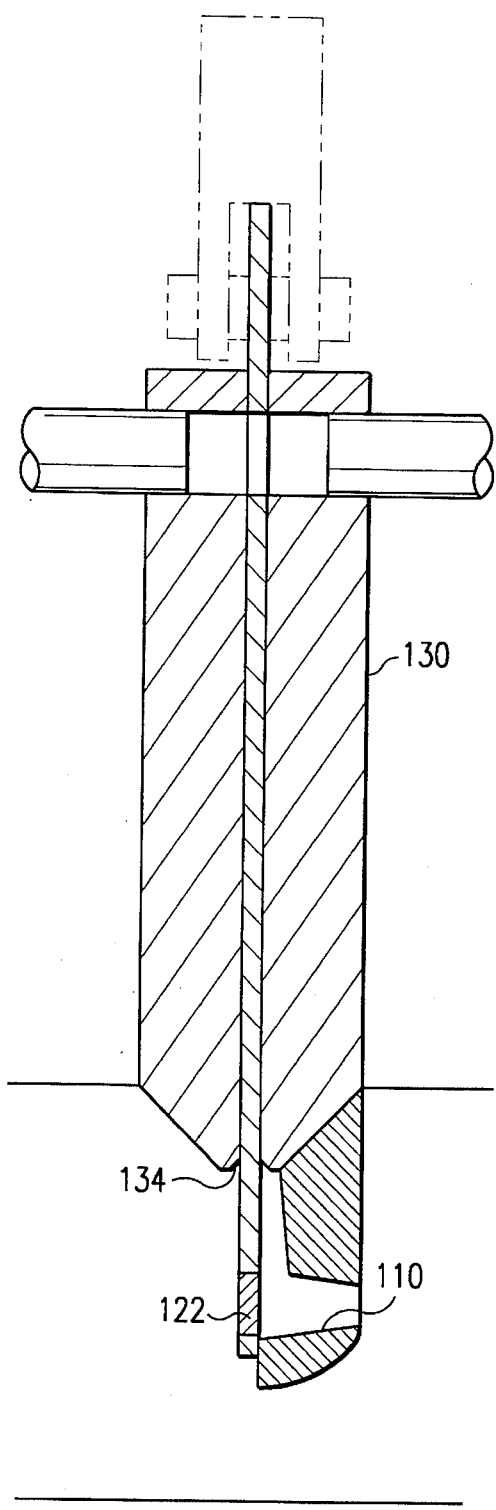
FIG. 2 is a cross-sectional view of the sleeve and probe member.
Figure 3:
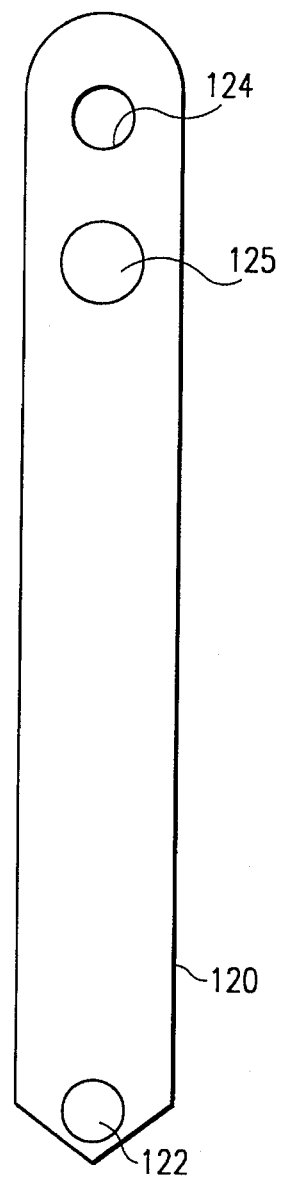
FIG. 3 is a schematic of the probe member.

Referring first to FIG. 1, a system is shown which utilizes an apparatus for optically analyzing a sample by a transmission approach. As illustrated in FIG. 1, the probe member (120) obtains a sample of the fluid as the fluid passes through the distal end of the probe member (120) having an aperture (122) as shown in FIG. 3 to retain a sample of the fluid. The proximate end of the probe member (120) has an aperture (124) as shown in FIG. 3 to be journaled to the member (163) allowing the probe to be moved within the sleeve (130). The probe member (120) further includes a transparent window (125) as shown in FIG. 3 to allow normalization of the spectrometer or other measuring device. The sleeve (130) as shown in FIGS. 1 and 2 surrounds the probe member (120) and includes an aperture (134) as shown in FIG. 2 positioned continuously through the longitudinal direction of the sleeve (130). Exemplary, the probe member (120) and the surface of the cylinder (150) formed by the center longitudinal aperture is Teflon (TM), for example FEP Teflon or polytetrofluroethylene of PTFE. The sleeve (130) has a pair of incline surfaces (132). The sleeve (130) and the probe member (120) could be made from Teflon coated stainless steel to meet sanitary standards of the food industry. One of the incline surfaces (132) engages a mandrel (100) by a 2 inch Triclover-style (TM) clamp, for example, to support the probe member (120) against the flow of the fluid. The mandrel (100) includes an aperture (110) parallel to the radial direction of the sleeve (130) and is designed to minimize the restriction of the flow. The aperture is decreasingly tapered in the downstream direction of the fluid.

As illustrated in FIGS. 1 and 2, the sleeve includes a pair of radial slots (134) to mount the transmission apparatus of the light. For example, the transmission apparatus of the light could be a fiber-optic bundle. The transmission apparatus is isolated from direct contact with the supply of sample, avoiding the surface effect of the prior art.

A cylinder (150) has a center longitudinal aperture to compress the inwardly slanting member (136); the inwardly slanting member (136) slides along the sleeve (130) to compress the sleeve (130). The cylinder includes an aperture which has external threads to engage the threads of bolt (140) which is internally threaded.

The cylinder has a flange (152) at one end of the cylinder (150) to engage a flange of the conduit (160), which conducts the fluid. A connecting arm (160) connects the probe member (120) to the arm (170). The connecting arm (160) has a slot to couple the probe member (120) by a member (163). The member (163) is journaled to the connecting arm (160).

An actuator (170), for example, a ¾ inch diameter 4 inch stroke pneumatic cylinder moves the connecting arm (160) and in turn moves the probe member (120) within the aperture (134) of the sleeve.

The spectrometer make a measurement of a "empty cell" using the transparent window (125) and compensate from spectrometer materials. This empty cell or window could include, for example, a glass or plastic which would meet the sanitary requirements of the food industry.

When the fluid is very viscous with respect to water, such as cheese, the fluid sample remains in the aperture (122) so that it may be moved to the position adjacent to the fiber-optic bundles. When the sample is positioned adjacent to pair of fiber-optic bundles, light passes through the bundle and through the cheese sample allowing the sample to be optically analyzed.

FIG. 2 illustrates an additional embodiment in which the sleeve (130) includes a pair of externally inclined surfaces and a pair of internally facing incline surfaces.

The operation of the system is now described. The probe member (120) is initially at a lower position so that the aperture (122) of the probe member is within the conduit (160), which contains a fluid such as cheese. The probe member (120) is positioned such that the cheese flows through the aperture (122) and through the aperture (110) of the mandrel (100). The actuator (170) is raised, raising the probe member (120) into the sleeve (130) through the aperture (134) of the sleeve (130). The aperture (122) is raised until the aperture (122) is adjacent to the pair of fiber-optic bundles which are placed in the slots (134). The sample of the fluid remains in the aperture (122), allowing light to pass through the fiber-optic bundles and through the sample, and allowing accurate measurements of the sample to be taken. The present invention provides a fresh sample since no or little remnants of the previous sample remain in the aperture (122). The aperture is cleared of the sample of this action of the Teflon coated sleeve (130) and the aperture (122).

When an additional sample is to be taken, the probe member (120) is lowered into the conduit (160); the action of the aperture (122) with the sleeve will remove the old sample.

The arm (170) is controlled by the air-pressure regulator (180) and the results of the sample are analyzed by the meter (190) to measure the properties of the sample.

The present invention is easily disassembled for cleaning and withstands manual cleaning and handling without distorting the results. The spectrometer can be normalized or calibrated by positioning the transparent window 125 adjacent to the pair of fiber optic bundles in slots (134). The spectrometer can eliminate variations in illumination and compensate for distortions and aging of system components.

OTHER EMBODIMENTS

Although the present invention and its advantages have been described in detail, it should be understood that various changes, substitutions and alterations can be made herein without departing from the spirit and scope of the invention as defined by the appended claims.

What is claimed is:

1. A probe assembly for sampling a sample of a fluid, comprising:

and longitudinal member having a first aperture to receive and hold said sample of the fluid at a first position and a second aperture being a transparent window for normalization with a light transmission apparatus at a second position;

a sleeve having an aperture to slidably engage said longitudinal member, said sleeve having slots for positioning said light transmission apparatus and wherein said second aperture aligns with said slots for said normalization with said light transmission apparatus; and means for sliding said longitudinal member between said first position where said first aperture receives said sample and said second position where said first aperture aligns with said slots.

2. A probe assembly as in claim 1, wherein the probe assembly further comprises a cylinder for compressing said sleeve.

3. A probe assembly as in claim 2, wherein the cylinder includes a flange operable to engage a conduit to guide said fluid.

4. A probe assembly as in claim 3, wherein the cylinder includes a bolt to engage said cylinder.

5. A probe assembly as in claim 1, wherein the sleeve includes a mandrel coupled to and to support said longitudinal member.

6. A probe assembly as in claim 5 wherein the mandrel includes an aperture to allow the fluid to flow past the longitudinal member.

7. A probe assembly as in claim 1, wherein the longitudinal member is slidably engaged to the sleeve so that said first aperture may be positioned adjacent to said light transmission apparatus to obtain a measurement from said fluid.

8. A method for using a probe assembly, comprising the steps of:

providing a longitudinal member having a first aperture to receive and hold a sample at a and a second aperture having a transparent window for normalization with a pair of fiber-optic bundles;

providing a sleeve having a third aperture to slidably engage the longitudinal member along a longitudinal axis of said probe assembly; and sliding said longitudinal member let between a first position where said first aperture receives the sample and a second position where said second aperture aligns with said third aperture for said normalization and where said first aperture aligns with said third aperture.

* * * * *